(12) United States Patent
Sung et al.

(10) Patent No.: US 7,193,697 B2
(45) Date of Patent: Mar. 20, 2007

(54) APPARATUS FOR FEATURE DETECTION

(75) Inventors: Hsin-Yueh Sung, Taoyuan Hsien (TW); Bing-Shien Chung, Taoyuan Hsien (TW); Wen-Chi Lo, Taoyuan Hsien (TW); Chin-Chiang Liao, Taoyuan Hsien (TW); Miao-Shen Liu, Taoyuan Hsien (TW)

(73) Assignee: Chroma Ate Inc. (TW)

( * ) Notice: Subject to any disclaimer, the term of this patent is extended or adjusted under 35 U.S.C. 154(b) by 0 days.

(21) Appl. No.: 11/188,423

(22) Filed: Jul. 25, 2005

(65) Prior Publication Data

US 2007/0019186 A1 Jan. 25, 2007

(51) Int. Cl.
*G01N 21/00* (2006.01)

(52) U.S. Cl. .............. 356/237.1; 356/239.3; 356/239.2; 356/239.8; 356/237.3

(58) Field of Classification Search ......... 356/237.1, 356/239.2–239.3, 239.8, 237.3, 317; 250/231.13, 250/225

See application file for complete search history.

(56) References Cited

U.S. PATENT DOCUMENTS

| 4,806,776 | A | * | 2/1989 | Kley | 250/559.24 |
| 2003/0210391 | A1 | * | 11/2003 | Uto et al. | 356/237.1 |
| 2003/0218125 | A1 | * | 11/2003 | Igaki et al. | 250/231.13 |

* cited by examiner

*Primary Examiner*—Layla Lauchman
*Assistant Examiner*—Tri Ton
(74) *Attorney, Agent, or Firm*—Brooks Kushman P.C.

(57) ABSTRACT

An apparatus for feature detection of a test object includes at least one light source module and at least one image capturing unit. The light source module provides light to illuminate a test region of the test object, and includes a substrate, a set of light-emitting components, and a light-focusing unit. The light-emitting components are mounted on the substrate for emitting light in parallel directions that are generally transverse to the substrate. The light-focusing unit is to be disposed between the light-emitting components and the test object, receives the light emitted by the light-emitting components, and focuses the light on the test region of the test object. The image capturing unit captures an image of the test object at the test region.

9 Claims, 4 Drawing Sheets

APPARATUS FOR FEATURE DETECTION

BACKGROUND OF THE INVENTION

1. Field of the Invention

The invention relates to an apparatus for feature detection of a test object, more particularly to a simple and low cost apparatus for feature detection of a test object.

2. Description of the Related Art

Automated optical inspection is used during the manufacture of printed circuit boards and the like. During an automated surface mounting process, an automated optical inspection system is used to verify features of mounted electric components. A conventional automated optical inspection system generally includes an image capturing device to be disposed above a target printed circuit board and operable so as to capture images of test regions of the target printed circuit board, a moving device for generating relative movement between the image capturing device and the target printed circuit board, and a computerized control device for controlling the operation of the moving device and for analyzing the images captured by the image capturing device so as to verify the features of the test regions of the target printed circuit board. The image capturing device used in automated optical inspection systems usually includes a light source module and an image capturing module.

Features of printed circuit boards, which require verification, include edges of electric components, metal traces, and solder contacts. It is noted that these features can be simultaneously captured in an image only when light from the light source module illuminates the printed circuit board at a certain angle relative to the image capturing module. For example, if an electric component on the printed circuit board has a shiny surface that reflects light away from the image capturing module, the image capturing module would not be able to receive the reflected light from the electric component, and the area where the electric component is supposed to be in would appear black in the images captured by the image capturing module, thereby preventing the control device from successfully verifying the features of the printed circuit board.

Therefore, to create an image that is useful for automated inspection, illumination of the test regions by the light source module must be controlled relative to the image capturing module. To achieve this purpose, the light source module is generally designed to illuminate a test region of the printed circuit board from different angles, or to illuminate the test region from different combinations of angles.

In WO 02/01210 A1, there is disclosed an optical inspection system with an illumination system that includes substrates having serrations, and lighting elements (such as diodes that exhibit good beam radiation patterns) mounted on the serrations. The light emitting elements are focused on a focal point, and have different beam widths so that variations in illumination intensity as a function of elevation angle are reduced.

While the illumination system in WO 02/01210 A1 permits illumination of a test region from different angles or from different combinations of angles, formation of the serrations involves complex and precise manufacturing processes and equipment, which result in high production costs. In addition, such an illumination system cannot be flexibly configured.

SUMMARY OF THE INVENTION

Therefore, the object of the present invention is to provide an apparatus for feature detection that can overcome at least one of the aforesaid drawbacks of the prior art.

Accordingly, an apparatus of the present invention is adapted for feature detection of a test object, and comprises at least one light source module and at least one image capturing unit. The light source module provides light to illuminate a test region of the test object, and includes a substrate, a set of light-emitting components, and a light-focusing unit. The light-emitting components are mounted on the substrate for emitting light in parallel directions that are generally transverse to the substrate. The light-focusing unit is to be disposed between the light-emitting components and the test object, receives the light emitted by the light-emitting components, and focuses the light on the test region of the test object. The image capturing unit captures an image of the test object at the test region.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
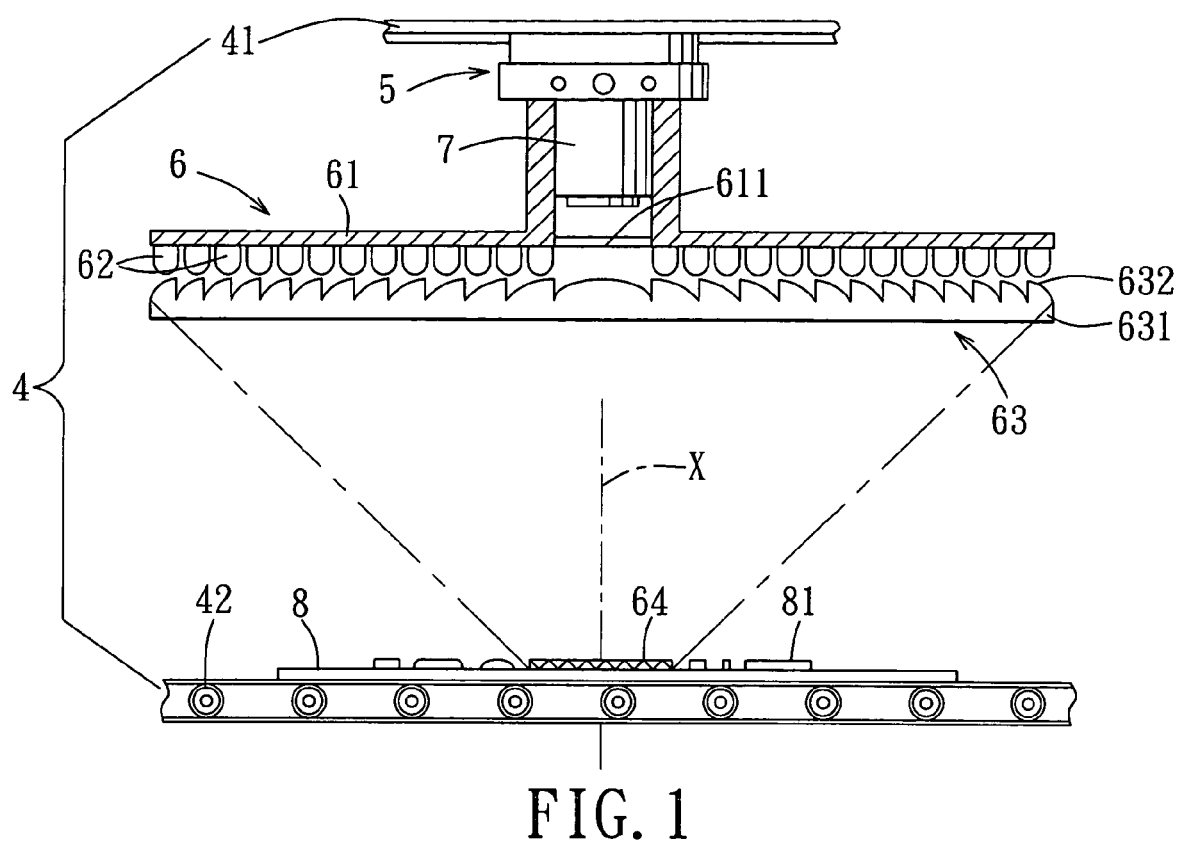
FIG. 1 is a schematic view of the first preferred embodiment of an apparatus for feature detection of a test object according to the present invention.

Before the present invention is described in greater detail with reference to the accompanying preferred embodiments, it should be noted herein that like elements are denoted by the same reference numerals throughout the disclosure.

Referring to FIG. 1, the first preferred embodiment of an apparatus for feature detection according to the present invention is shown to be adapted for inspecting a surface of a test object 8 in order to collect and analyze two-dimensional features of the test object 8. The surface of the test object 8 is perpendicular to a reference line (X). In this embodiment, the test object 8 is exemplified as a printed circuit board having electric components 81, such as capacitors, resistors, integrated circuits, etc., mounted on a surface thereof. The apparatus includes a moving module 4, a control module 5, a light source module 6, and an image capturing unit 7.

The moving module 4 is used to generate relative movement of the control module 5, the light source module 6 and the image capturing unit 7 at a predetermined height with respect to the test object 8. The moving module 4 includes a platform 41 for moving the control module 5, the light source module 6 and the image capturing unit 7, and a conveyor 42 for moving the test object 8. In this embodiment, the light source module 6 is spaced apart from the conveyor 42 at a distance ranging between twenty to thirty centimeters.

The light source module 6 provides light to illuminate a test region 64 of the test object 8 on the conveyor 42, and includes a substrate 61, a set of light-emitting components 62, and a light-focusing unit 63. In this embodiment, the substrate 61 is a printed circuit board formed with a through hole 611. The light-emitting components 62 are mounted on the substrate 61 for emitting light in parallel directions that are generally transverse to the substrate 61. In this embodiment, each of the light-emitting components 62 is a light-emitting diode. Since current light-emitting diodes exhibit good beam radiation patterns, the light emitted by the light-emitting components 62 travels in directions generally traverse to the substrate 61. The light-focusing unit 63, which is disposed between the light-emitting components 62 and the conveyor 42, receives the light emitted by the light-emitting components 62, and focuses the light on the test region 64 of the test object 8 on the conveyor 42.

Figure 2:
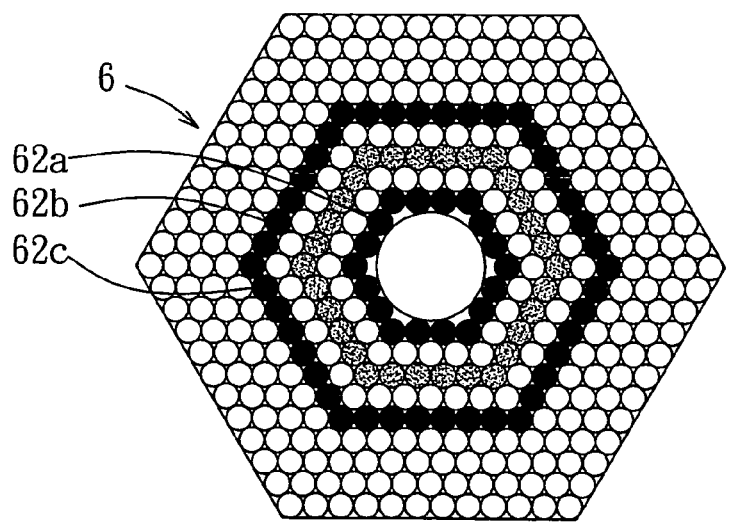
FIG. 2 is a schematic diagram of a light source module of the first preferred embodiment.

As shown in FIGS. 1 and 2, the light-emitting components 62 emit different colors of light, and are arranged on the substrate 61 in groups according to the colors of light emitted thereby. In this embodiment, the light-emitting components 62 include a first group 62a for emitting a first color (e.g., red) of light, a second group 62b for emitting a second color (e.g., green) of light, and a third group 62c for emitting a third color (e.g., blue) of light. The light-emitting components 62 are arranged on the substrate 61 in concentric annular groups according to the colors of light emitted thereby, and are operable so as to form a full spectrum of projected light.

In this embodiment, the light-focusing unit 63 includes a Fresnel lens having a thin resin plate 631, and a Fresnel pattern 632 formed on the resin plate 631 for diffracting light that passes therethrough. Fresnel lenses are advantageous over other conventional light-focusing lenses in view of their higher light transmissibility, lighter weight and larger illuminating area characteristics. Fresnel lenses are currently in wide use in home projectors for focusing light to be projected on screens. Since the Fresnel lens is used in this embodiment to focus light emitted by the light-emitting components 62 to the test region 64 of the test object 8, it is no longer needed to dispose the light-emitting components 62 at different angles relative to the test object 8 as taught in the conventional automated optical inspection systems.

In this embodiment, the image capturing unit 7 is located in the through hole 611 of the substrate 61, and is to be aligned with the reference line (X) passing through the test region 64 of the test object 8 so as to capture an image of the test object 8 at the test region 64. In the preferred embodiment, the image capturing unit 7 includes a color camera available from CIS Corporation. The image capturing unit 7 further includes an image control circuit to convert captured images into standard color video signals (such as NTSC signals). The color video signals are then provided to the control module 5 for image collection and analysis.

The control module 5 is coupled to the moving module 4 for controlling operations of the platform 41 and the conveyor 42 so as to generate relative movement between the light source module 6 and the test object 8 while the light source module 6 is disposed at a predetermined height from the test object 8. The control module 5 is further coupled to the light source module 6 for controlling operation of the light-emitting components 62, such as for light mixing. The control module 5 is additionally coupled to the image capturing unit 7 for image collection and analysis. In this embodiment, the control module 5 includes a single microprocessor coupled to the moving module 4, the light source module 6 and the image capturing unit 7. In other embodiments, the control module 5 includes two microprocessors, one of which is responsible for controlling operations of the moving module 4 and the light source module 6, and the other one of which is responsible for image collection and analysis.

When this embodiment is applied for feature detection of a printed circuit board, the control module 5 analyzes the captured images by comparing the captured images from the image capturing unit 7 with reference component parameters of a standard printed circuit board that were established beforehand in the control module 5. When the light-emitting components 62 are operated to emit monochromatic light for illuminating the test object 8, the control module 5 is able to detect whether there is an electric component 81 missing from or has a missing solder connection with the printed circuit board 8 by comparing the captured images with the pre-established reference data in the control module 5. On the other hand, when the light-emitting components 62 are operated to emit different colors of light for illuminating the test object 8, the control module 5 is capable of further obtaining chromatic information associated with the test object 8.

Figure 3:
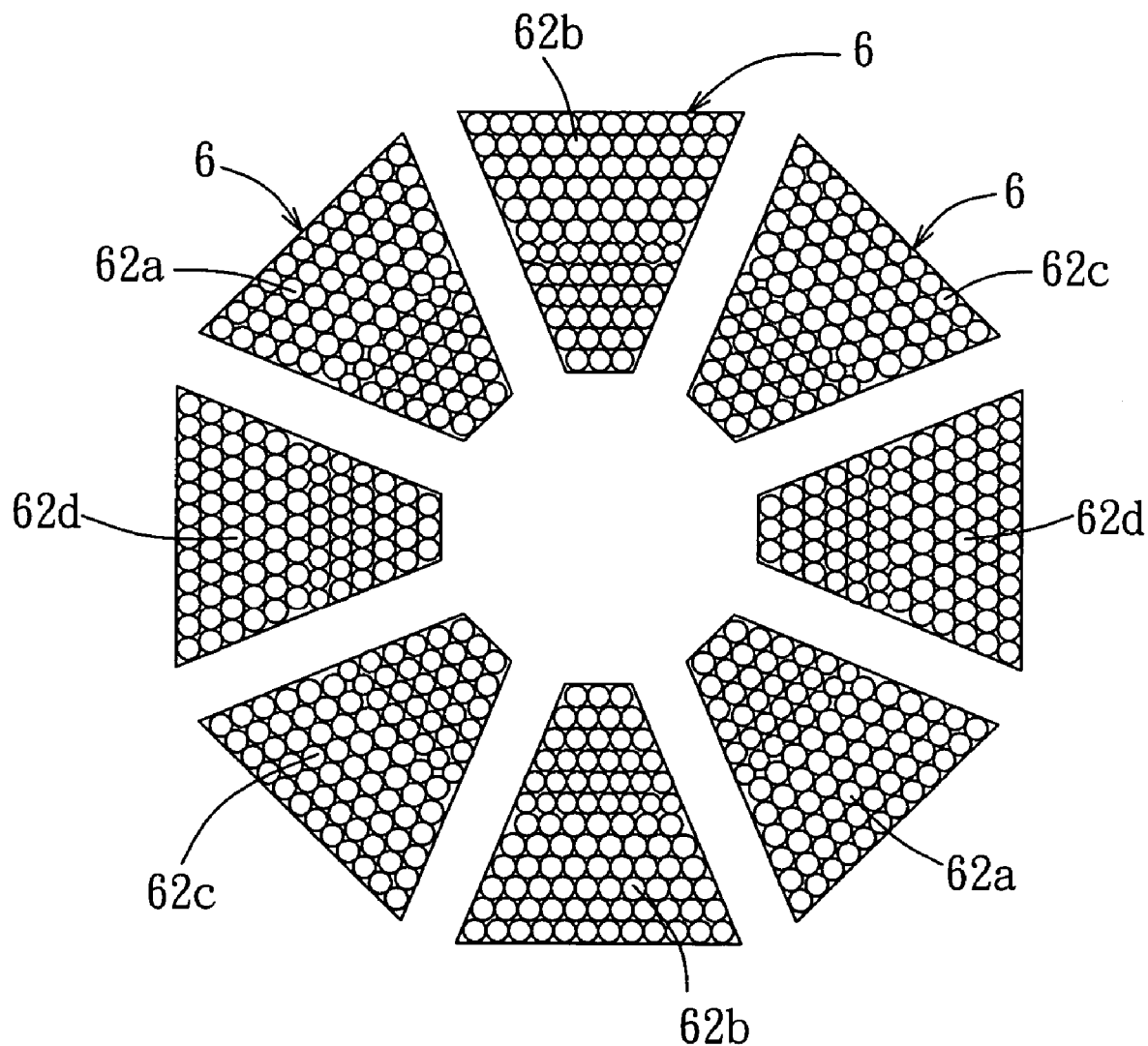
FIG. 3 is a schematic diagram of a light source module of the second preferred embodiment of an apparatus for feature detection according to the present invention.
Figure 4:
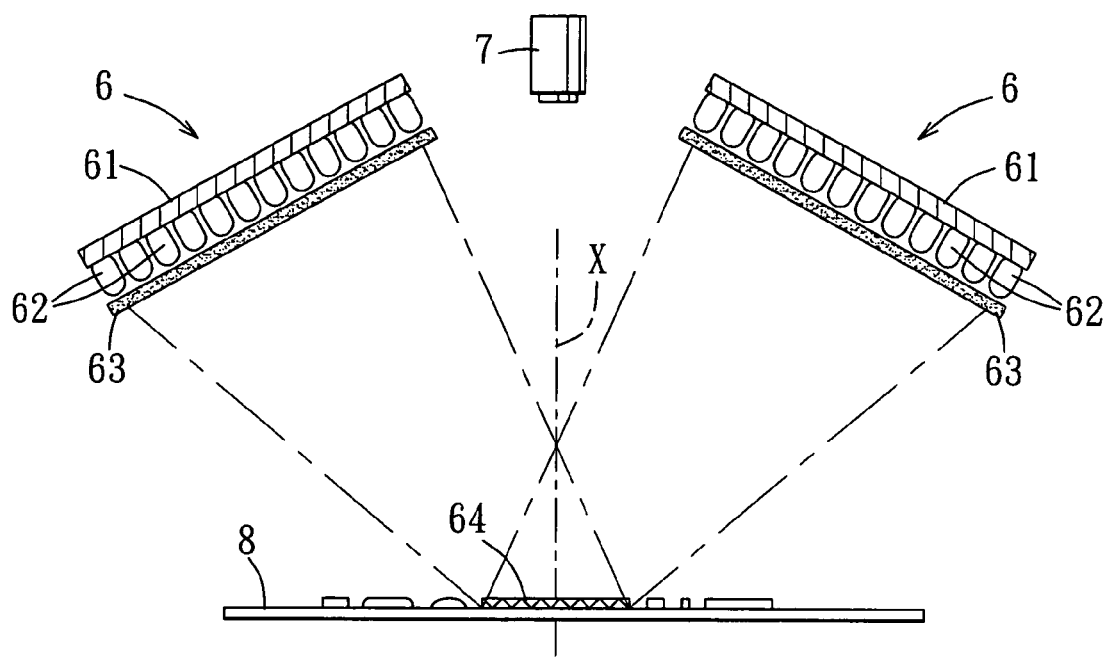
FIG. 4 is a schematic view of the second preferred embodiment.

Referring to FIGS. 3 and 4, the second preferred embodiment of this invention is shown to differ from the previous embodiment in that the apparatus of this embodiment includes a plurality of light source modules 6 (there are eight light source modules 6 in this embodiment) that are disposed at different angles relative to the reference line (X) that passes through the test region 64 of the test object 8. The light-emitting components 62 on the same one of the substrates 61 of the light source modules 6 emit the same color of light, whereas the light-emitting components 62 on different ones of the substrates 61 of the light source modules 6 emit different colors of light. In particular, the light-emitting components 62 of the light source modules 6 include two first groups 62a for emitting a first primary color of light, two second groups 61b for emitting a second primary color of light, two third groups 61c for emitting a third primary color of light, and two fourth groups 61d for emitting a fourth mixed color of light. Therefore, this embodiment permits illumination of the test region 64 using different colors of light from different angles, as well as illumination of the test region 64 using the same color of light but from different combinations of angles.

Figure 5:
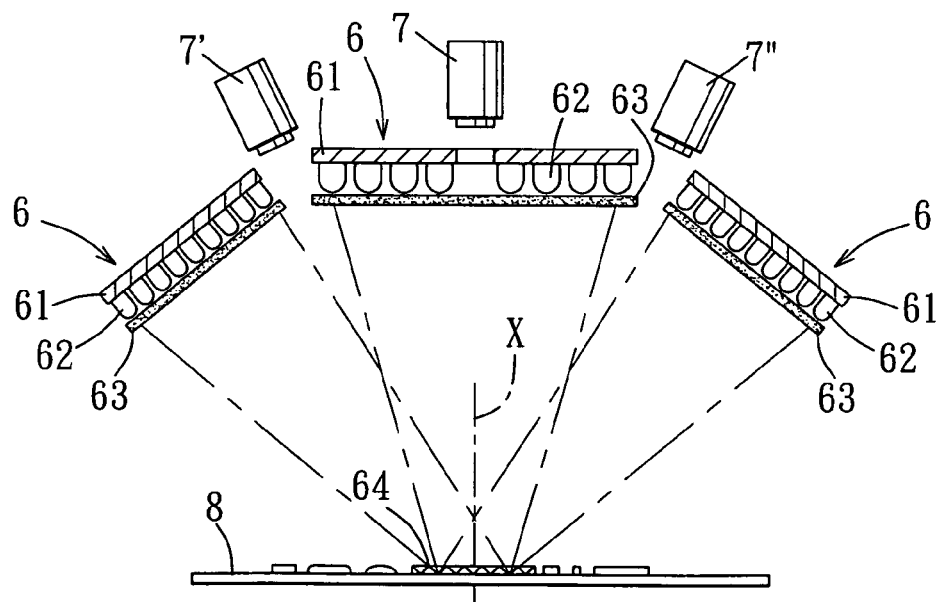
FIG. 5 is a schematic view of the third preferred embodiment of an apparatus for feature detection of a test object according to the present invention.

Referring to FIG. 5, the third preferred embodiment of this invention is shown to differ from the second preferred embodiment in that the apparatus of this embodiment further includes a plurality of image capturing units 7, 7', 7" that are disposed at different angles relative to the test object 8. In this embodiment, one of the image capturing units 7 is to be aligned with the reference line (X) that passes through the test region 64 of the test object 8, whereas the other two image capturing units 7', 7" are inclined with respect to the reference line (X). Hence, images of the test object 8 at the test region 64 are captured at different viewing angles through the image capturing units 7, 7', 7". Thereafter, the control module 5 (see FIG. 1) calculates the heights of the electric components 81 (see FIG. 1) on the test object 8 from the images captured at the different viewing angles.

It is noted that during the process of soldering electric components 81, there are errors that cannot be located by merely viewing from the top or one side of electric components 81. Examples of such errors include: soldering failure due to upwardly bent terminal end of a tombstone component, dimensions of a damaged part of a component exceed preset thresholds, etc. These errors are revealed only through component height analysis.

Accordingly, by increasing the number of image frames, more component data is available for inspection, thereby promoting the reliability of verification results.

Moreover, while commercially available light-emitting diodes have a response time of about 50 microseconds, the response time of commercially available monochromatic or color cameras is only about 1/30 second to comply with the NTSC standard. Hence, the frame refresh rate is 30 per second. In other words, although the light source module 6 is able to provide different angles and different color combinations of light within 1/30 second, the monochromatic or color cameras are only able to capture one monochromatic or color image every 1/30 second.

Therefore, in order to overcome the aforesaid inspection speed restriction imposed by the image capturing units 7, 7', 7", it is contemplated in this embodiment that the control module 5 controls respective operations of the image capturing units 7, 7', 7" at specific time intervals when capturing monochromatic or color images. For instance, the control module 5 first controls the light source module 6 to illuminate the test object 8 at a first angle using a first light output, and controls the image capturing unit 7 to capture a first monochromatic or color image. After 50 microseconds, the control module 5 controls the light source module 6 to illuminate the test object 8 at a second angle using a second light output, and controls the image capturing unit 7' to capture a second monochromatic or color image. After another 50 microseconds, the control module 5 controls the light source module 6 to illuminate the test object 8 at a third angle using a third light output, and controls the image capturing unit 7" to capture a third monochromatic or color image. Then, 1/30 second after, the above procedure is repeated to result in a faster inspection speed.

It is apparent to those skilled in the art that the number of image capturing units 7, 7', 7" is not limited to three, and can be increased in actual practice to result in a corresponding increase in the number of viewing angles and in a faster inspection speed.

Figure 6:
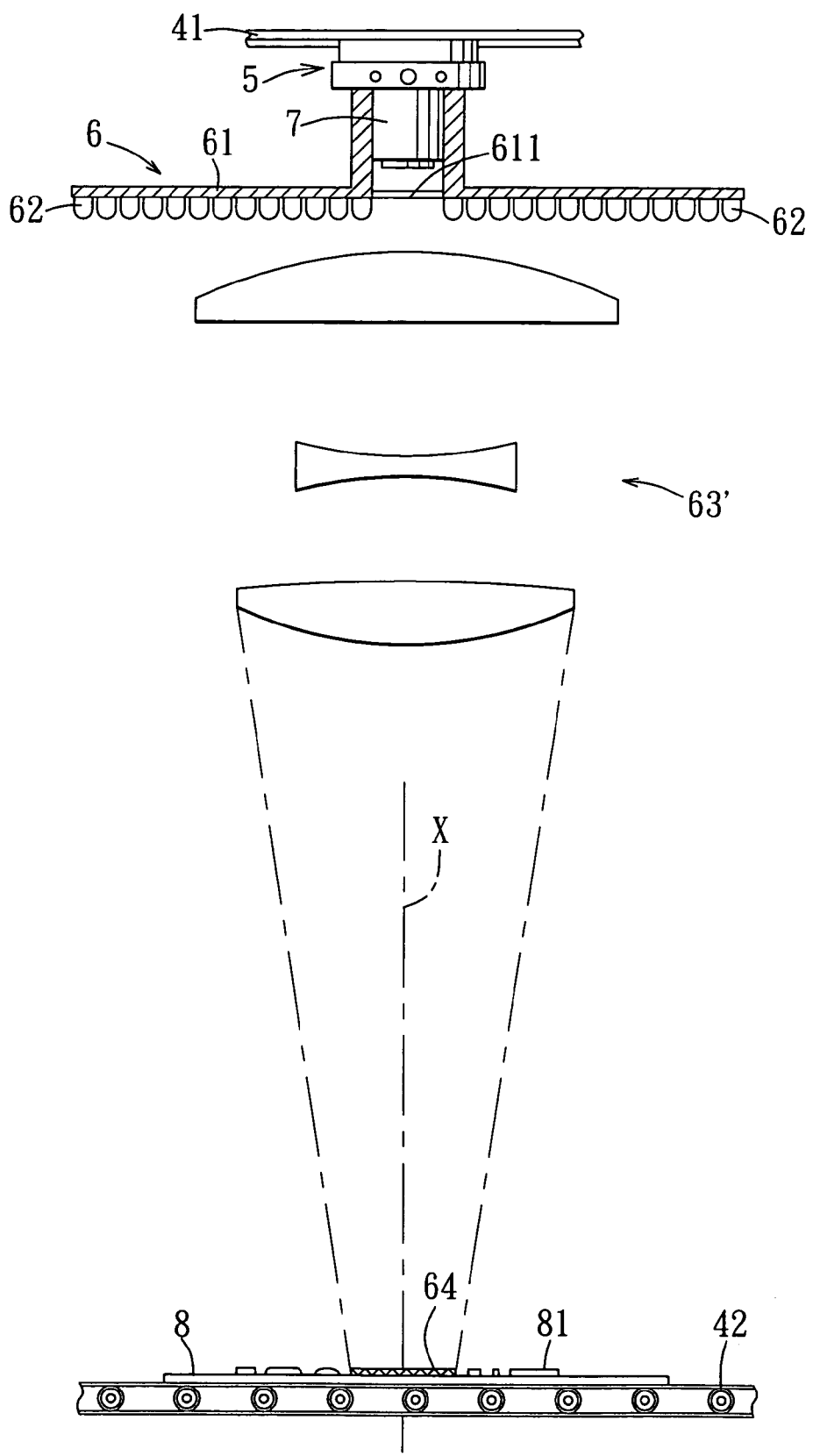
FIG. 6 is a schematic view of the fourth preferred embodiment of an apparatus for feature detection of a test object according to the present invention.

Referring to FIG. 6, the fourth preferred embodiment of this invention is shown to differ from the first preferred embodiment mainly in the configuration of the light-focusing unit 63'. In this embodiment, the light-focusing unit 63' includes an optical lens set, which is made from optical plastics or glass. Like the Fresnel lens employed in the first preferred embodiment, the light-focusing unit 63' is also able to focus light emitted in parallel by the light-emitting components 62 to the test region 64 of the test object 8. By adjusting positions of optical components of the light-focusing unit 63' in a manner well known to those skilled in the art, the illuminated area of the test region 64 can be adjusted accordingly. Moreover, the light-focusing unit 63' can be configured to provide extra functions, such as image correction and ensuring uniform illuminating light.

In view of the light-focusing unit 63, 63' in the light source module 6 of the apparatus of this invention, the structure of the apparatus of this invention is simplified to result in a simple and low cost manufacturing process for the same.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

We claim:

1. An apparatus for feature detection of a test object, said apparatus comprising:
    at least one light source module for providing light to illuminate a test region of the test object, said light source module including a substrate, a set of light-emitting components mounted on said substrate for emitting light in parallel directions that are generally transverse to said substrate, said light-emitting components emitting different colors of light and being arranged on said substrate in groups according to the colors of light emitted thereby, and a light-focusing unit disposed between said light-emitting components and the test object, said light-focusing unit receiving the light emitted by said light-emitting components and focusing the light on the test region of the test object; and
    at least one image capturing unit for capturing an image of the test object at the test region.

2. The apparatus as claimed in claim 1, wherein said light-focusing unit includes a Fresnel lens.

3. The apparatus as claimed in claim 1, wherein said light-focusing unit includes an optical lens set.

4. The apparatus as claimed in claim 1, wherein said light-emitting components are arranged on said substrate in annular groups according to the colors of light emitted thereby.

5. The apparatus as claimed in claim 1, comprising at least two of said image capturing units that are disposed at different angles relative to the test object.

6. The apparatus as claimed in claim 1, wherein each of said light-emitting components is a light-emitting diode.

7. The apparatus as claimed in claim 1, wherein said substrate is a printed circuit board.

8. The apparatus as claimed in claim 1, further comprising a control module coupled to said light source module for controlling operation of said light-emitting components, and coupled to said image capturing unit for image collection and analysis.

9. An apparatus for feature detection of a test object, said apparatus comprising:
    at least two light source modules for providing light to illuminate a test region of the test object and the light sources being disposed at different angles relative to the test object, each light source module including: a substrate, a set of light-emitting components mounted on said substrate for emitting light in parallel directions that are generally transverse to said substrate, and a light-focusing unit disposed between said light-emitting components and the test object, each light-focusing unit receiving the light emitted by said light-emitting components and focusing the light on the test region of the test object, wherein said light-emitting components of each light source module emit the same color of light which is different from the color of light emitted from the light emitting components of each other light source module; and
    at least one image capturing unit for capturing an image of the test object at the test region.

* * * * *